United States Patent [19]

Le Bras-Roulier et al.

[11] Patent Number: 5,814,311

[45] Date of Patent: Sep. 29, 1998

[54] COSMETIC COMPOSITION IN THE FORM OF A COMPACT POWDER AND PROCESS FOR PREPARING IT

[75] Inventors: Veronique Le Bras-Roulier, Paris; Myriam Mellul, L'Hay-Les-Roses, both of France

[73] Assignee: L'Oreal, Paris, France

[21] Appl. No.: 561,862

[22] Filed: Nov. 22, 1995

[30] Foreign Application Priority Data

Nov. 24, 1994 [FR] France .................................. 94 14110

[51] Int. Cl.$^6$ ...................................... A61K 7/021
[52] U.S. Cl. ............................. 424/69; 424/63; 424/401; 514/844
[58] Field of Search ................................ 424/69, 401, 63; 514/844

[56] References Cited

U.S. PATENT DOCUMENTS

| | | |
|---|---|---|
| 5,206,012 | 4/1993 | Farer et al. . |
| 5,219,561 | 6/1993 | Gaghebien et al. . |
| 5,486,354 | 1/1996 | Defossez et al. ........................ 424/63 |
| 5,496,544 | 3/1996 | Mellul et al. ....................... 424/78.03 |
| 5,582,818 | 12/1996 | Nakanishi et al. ....................... 424/59 |
| 5,628,934 | 5/1997 | Ohno et al. ........................... 252/586 |

FOREIGN PATENT DOCUMENTS

| | | |
|---|---|---|
| 0447286A1 | 2/1991 | European Pat. Off. . |
| 0447287A1 | 2/1991 | European Pat. Off. . |
| 0605284A1 | 12/1993 | European Pat. Off. . |

*Primary Examiner*—Robert H. Harrison
*Attorney, Agent, or Firm*—Finnegan, Henderson, Farabow, Garrett & Dunner, L.L.P.

[57] ABSTRACT

The invention relates to a cosmetic composition in the form of a compact powder comprising a fatty phase and a pulverulent phase, said pulverulent phase comprising a first incompatible filler and at least a second filler which may be compactible or incompactible, these two fillers being of different types. The composition preferably has an internal porosity of greater than 2 $m^2/g$. The composition is obtained by preparing an oil-in-water type emulsion of the fatty phase in an aqueous phase, dispersing the pulverulent phase in the emulsion, casting the dispersion obtained in a mould, and freeze drying the dispersion.

33 Claims, No Drawings

COSMETIC COMPOSITION IN THE FORM OF A COMPACT POWDER AND PROCESS FOR PREPARING IT

The present invention relates to a composition, especially a cosmetic composition, in the form of a compact powder comprising a fatty phase and a pulverulent phase, it being possible for the composition to be used as a make-up product.

The invention also relates to the process for manufacturing the composition.

Some cosmetic compositions, such as foundation, eyeshadow, or blusher, are provided in the form of compact powder generally consisting of a fatty binder and a pulverulent phase containing pigments and/or fillers.

Some cosmetic compositions comprise, in addition, a small quantity of so-called incompactible filler, especially microspheres of low density, because such a filler confers on the composition a very smooth and non-greasy feel. Incompactible filler is understood to mean a raw material which, above a certain percentage which will depend on the material in question, cannot be compacted by means of a mechanical press.

The compositions of the prior art comprising these small quantities of incompactible fillers can have, however, certain drawbacks: the integrity of the compacted product obtained is not good during its storage, the compacted product does not have sufficient resistance to shock, and/or the compacted product does not have a satisfactory flat surface.

For example, in the prior art compositions, when the compacted product comprises hollow microspheres made of thermoplastic material with a density of less than 0.1 g/cm$^3$, the appearance of the onset of fragmentation and of breaking-up is observed when the percentage of microspheres is greater than about 1% by weight; this degradation is the result of relaxation phenomena.

Various solutions have been proposed in order to overcome the above disadvantages. In EP 486 639, it is proposed to mix a pulverulent phase and a binder in a nonaqueous solvent, to distribute the fluid paste obtained in appropriate moulds and then to evaporate the solvent. The particulate phase contains microspheres comprising one or more cavities which are open or closed so as to avoid any withdrawal. This process has several disadvantages. For example, the solvents are often toxic and thus should not be handled. Furthermore, the finished product should not contain traces of solvent. On the other hand, the fact that nonaqueous solvents are used prevents the use of water-soluble active agents, such as, for example. humectants.

In EP 447 286, a binder and a pulverulent phase containing 0.02–5% of hollow microspheres made of thermoplastic material having a density of less than 0.1 g/cm$^3$ and sizes of less than 30 μm are introduced into a mechanical press. However, for quantities of microspheres greater than 1%, problems of integrity of the compacted product during storage and problems of homogeneity of the distribution of the binder in such a filler volume appear. Now, it is for proportions greater than 1% that truly novel cosmetic qualities are obtained. Furthermore, with microspheres of sizes greater than 30 μm, a relaxation phenomenon is observed which causes fragmentations in the compacted product.

In JP-A 62 53914, a process is described which consists of preparing an aqueous mixture of cosmetic powders and a water-soluble macromolecular compound as binder, casting the mixture in a mould, and freeze-drying it. A moulded product of arbitrary shape, but whose cosmetic qualities are not sufficient, is thus obtained.

The aim of the present invention is to overcome the disadvantages of the prior art and to propose a composition in the form of a compact powder that is stable to storage and has a good cohesion while containing a quantity of incompactible fillers which may be high.

The composition obtained is also solid, that is to say is resistant to shock, and has a flat and smooth surface. Even though the composition can be referred to as solid, a preferred advantage of the present invention is that the composition possesses a porous network, which will be discussed in greater detail below.

The subject of the present invention is a composition in the form of a compact powder comprising a fatty phase and a pulverulent phase, said pulverulent phase comprising a first incompactible filler and at least a second filler, said first and said second fillers being selected from inorganic lamellar fillers, organic lamellar fillers, inorganic spherical fillers, and organic spherical fillers, said first and second fillers being of different types.

The subject of the present invention is also a process for preparing said composition in which the pulverulent phase is dispersed in an oil-in-water type emulsion of the fatty phase in an aqueous phase, the dispersion obtained is cast in a mould, and said dispersion is freeze-dried.

One advantage of the invention is to allow the production of a composition capable of being provided in diverse and varied, or even complex, forms which were difficult to obtain reproducibly according to the prior state of the art.

Indeed, according to a first prior art technique, pulverulent fillers are moulded in a press in the presence of a binder, but it is then difficult to obtain a constant pressure at all points of the mould if the mould has a complicated shape; consequently, the compact powder obtained has fragile zones. According to the second prior art technique, a mixture in the form of a fluid paste comprising a binder is cast in a mould; when the paste is prepared by mixing with water, withdrawal phenomena appear during drying and the compact powder obtained is deformed and does not have a flat surface. The invention makes it possible to overcome these disadvantages and to obtain a composition of diverse shapes.

Another advantage of the invention is to allow the production of a composition having a new texture, of very smooth and non-greasy feel.

Another advantage of the invention is to allow the production of a composition having remarkable cosmetic qualities by virtue of the presence of at least two fillers of different types.

In the remainder of the present description, the percentages are given by weight, unless otherwise stated.

The composition according to the invention is therefore provided in the form of a compact powder comprising a fatty phase and a pulverulent phase.

The pulverulent phase comprises at least a first incompactible filler and at least a second filler, which may be compactible or incompactible, each filler being chosen from inorganic lamellar fillers, organic lamellar fillers, inorganic spherical fillers, and organic spherical fillers, said first and said second fillers being of different types.

Each type of filler makes it possible to offer special and different qualities to the composition according to the invention. Thus, for example, inorganic lamellar fillers generally offer smoothness, inorganic spherical fillers generally offer a good disintegration, and organic spherical fillers generally have a structuring role and offer smoothness. In order to obtain a composition having good cosmetic properties, it is therefore highly preferred to mix at least two fillers of different types.

Among the lamellar inorganic fillers, there may be mentioned:

- talcs or magnesium silicate hydrates, in the form of particles of sizes generally less than 40 μm;
- micas or aluminosilicates of varied compositions and which are preferably provided in the form of scales having sizes of 2 to 200 μm, more preferably 5–70 μm, and preferably a thickness of 0.1 to 5 μm, more preferably of 0.2–3 μm, it being possible for these micas to be of natural origin (for example muscovite, margarite, roscoelite, lipidolite, biotite) or of synthetic origin. They are generally transparent and make it possible to confer a satiny appearance on the skin;
- clays such as sericites, which belong to the same chemical and crystalline class as muscovite but whose organoleptic properties are similar to talc;
- kaolin or aluminium silicate hydrate, which is provided in the form of particles with isotropic forms having sizes generally less than 30 μm and which possess good fatty substance-absorbing properties;
- boron nitrides.

These fillers are generally compactible.

However, among these inorganic lamellar type fillers, some are incompactible. There may thus be mentioned:

- some talcs, such as "Talc K1" from the company NIPPON or "Talc Extra Steamic OOS" from the company LUZENAC;
- some sericites, such as "Sericite BC282" from the company WHITTAKER;
- most mica titaniums when they are used at a high percentage, among which there may be mentioned mica-nanotitanium "Coverleaf PC 2055M" from the company IKEDA.

Among the compactible organic lamellar fillers, there may be mentioned powders of tetrafluoroethylene polymers, such as "Fluon" from the company MONTEFLUOS, or "Hostaflonq" from the company HOECHST.

Among the incompactible organic lamellar type fillers, there may be mentioned the lauroyl lysine "Aminope LL-11" from the company AJINOMOTO.

Among the compactible inorganic spherical type fillers, there may be mentioned:

- zinc and titanium oxides, generally used in the form of particles having sizes not exceeding a few micrometres (or even less than 1 μm in the case of titanium oxide), in particular spherical titanium dioxides such as "SPHERITITAN" from the company IKEDA; these oxides have an unctuous feel, a good covering power and a high opacity;
- precipitated calcium carbonate which, in the form of particles of sizes greater than 10 μm, has an unctuous feel and makes it possible to obtain a matt appearance;
- magnesium carbonate and hydrocarbonate, which has especially perfume-fixing properties;
- non-porous spherical silica and
- hydroxyapatite.

Among the incompactible spherical inorganic type fillers, there may be mentioned:

- microspheres of silica with open porosity or, preferably, microspheres of hollow silica, such as "SILICA BEADS" from the company MAPRECOS, these microspheres being advantageously impregnated with a cosmetic active agent, and
- glass or ceramic microcapsules "MACROLITE" from the company 3M.

Among the compactible spherical organic type fillers, there may be mentioned:

- metallic soaps derived from carboxylic organic acids having 8 to 22 carbon atoms, preferably 12 to 18 carbon atoms, for example zinc, magnesium or lithium stearate, zinc laurate, and magnesium myristate; these soaps, generally present in the form of particles having sizes of less than 10 μm, have an unctuous feel and facilitate the adhesion of the powder to the skin;
- powders of non-expanded synthetic polymers, such as polyethylene, polyesters (for example polyethylene isophthalate or terephthalate), and polyamides (for example Nylon), in the form of particles having sizes of less than 50 μm, which possess absorbent properties and make it possible to confer a velvety appearance on the skin;
- spheronized powders of synthetic polymers, cross-linked or otherwise, such as polyamide powders such as the poly-β-alanine or Nylon powders, for example the "Orgasol" powder from the company ATOCHEM, polyacrylic or polymethacrylic acid powders, powders of polystyrene cross-linked with divinylbenzene, and powders of silicone resin; and
- powders of organic materials of natural origin such as maize, wheat or rice starches.

Among the incompactible spherical organic type fillers, there may be mentioned:

- microporous microspheres of polymers, which have a structure similar to that of a sponge; they have, in general, a specific surface area of at least $0.5$ $m^2/g$ and, in particular, of at least 1 $m^2/g$, the said specific surface area having no upper limit other than that resulting from the practical possibility of producing microspheres of very high porosity: the specific surface area may, for example, be as high as 1,000 $m^2/g$ or even more. There may be mentioned the microspheres of acrylic polymers, such as those in the form of a cross-linked acrylate copolymer "Polytrap" from the company DOW CORNING, and those of polymethyl methacrylate "MICROPEARL M" or "MICROPEARL M 100" from the company SEPPIC; these microporous microspheres may be advantageously impregnated, especially with cosmetic active agents: there may be mentioned, in this respect, the microspheres of styrene/divinylbenzene copolymers sold under the trade name "PLASTIC POWDER FPSQ" by the company TOSHIKI, which are impregnated with squalane which is an emollient cosmetic active agent;
- microcapsules of polymers which comprise a single closed cavity and form a reservoir, which may contain a liquid, especially a cosmetic active agent; they are prepared by known processes such as those described in U.S. Pat. No. 3,615,972 and EP-A 0 56219, the disclosures of which are specifically incorporated by reference herein. They can be produced, for example, from polymers or copolymers of acids, amines or esters, monomers with ethylene type unsaturation, urea-formaldehyde polymers, or from polymers or copolymers of vinylidene chloride.

By way of example, there may be mentioned the microcapsules made from polymers or copolymers of methyl acrylate or methacrylate, or alternatively from copolymers of vinylidene chloride and acrylonitrile; among the latter, there should be mentioned especially those which contain, by weight, 20–60% of units derived from vinylidene chloride, 20–60% by weight of units derived from acrylonitrile, and 0–40% by weight of other units such as units derived from an acrylic and/or styrene monomer.

There may also be used acrylic polymers or copolymers cross-linked, for example in the case of polymers comprising a carboxylic group, with diols serving as cross-linking agents. By way of example, there may be mentioned the microcapsules made of vinylidene chloride/acrylonitrile copolymer "EXPANCEL" from the company Kemanord Plast, the microcapsules "Q-MAX" from the company Q-MAX and the microcapsules "3M" from the company 3M.

The pulverulent phase may comprise 1–100% of incompactible fillers, preferably 60–100%, and 0–99% of compactible filler, preferably 0–40%, the said percentages being given relative to the pulverulent phase.

When the incompactible fillers have a very low density, especially of less than 0.1 g.cm$^{-3}$, they are preferably present in an amount of 2–10% relative to the final composition.

When the incompatible fillers have a density from 0.1 to 0.5 g.cm$^{-3}$, they are preferably present in an amount of 2–40% in weight relative to the weight of the final composition.

When the incompatible fillers have a higher density, especially greater than 0.5 g.cm$^{-3}$, they are preferably present in an amount of 30–90% in weight relative to the weight of the final composition.

The pulverulent phase may contain, in addition to the fillers, pigments, preferably in a quantity of 0–50% relative to the total weight of the final composition. These pigments may be chosen from inorganic pigments, organic pigments and pearlescent pigments.

Among the inorganic pigments, there may be mentioned, for example titanium dioxide (rutile or anatase), optionally surface-treated; black, yellow, red and brown iron oxides; manganese violet; ultramarine blue; optionally hydrated chromium oxide; and ferric blue.

Among the organic pigments, there may be mentioned for example the pigments D & C red, D & C orange, D & C yellow, carbon black, and the lakes based on carmine.

The pearlescent pigments may be chosen especially from the white pearlescent pigments such as mica coated with titanium oxide, bismuth oxychloride; the coloured pearlescent pigments such as mica titanium with iron oxides, mica titanium with ferric blue or chromium oxide, mica titanium with an organic pigment of the abovementioned type, as well as the pigments based on bismuth oxychloride.

The composition also comprises a fatty phase.

This fatty phase may comprise oils and/or waxes of animal, plant, inorganic or synthetic origin alone or as mixtures.

Among the oils which may be used, there may be mentioned vison oil, turtle oil, soya bean oil, grapeseed oil, sesame oil, maize oil, rapeseed oil, sunflower oil, cottonseed oil, avocado oil, olive oil, pasta oil, jojoba oil, groundnut oil; hydrocarbon oils such as paraffin oils, squalane, petroleum jelly; fatty esters, such as isopropyl myristate, isopropyl palmitate, butyl stearate, hexyl laurate, isononyl isononate, 2-ethylhexyl palmitate, 2-hexyldecyl laurate, 2-octyldecyl palmitate, 2-octyldodecyl myristate or lactate, 2-diethylhexyl succinate, diisostearyl malate, glycerin or diglycerin triisostearate; silicone oils such as polymethylsiloxanes, polymethylphenylsiloxanes, polysiloxanes modified by fatty acids, fatty alcohols or polyoxyalkylenes, fluorinated silicones, perfluorinated oils; higher fatty acids such as myristate acid, palmitic acid, stearic acid, behenic acid, oleic acid, linoleic acid, linolenic acid or isostearic acid; high fatty alcohols such as cetanol, stearyl alcohol or oleyl alcohol.

Among the waxes which may be used, there may be mentioned beeswaxes, lanoline waxes and Chinese waxes; Carnauba, Candelilla and ouricurry waxes, cork fibre waxes, sugar cane waxes, Japon waxes, hydrogenated jojoba waxes, hydrogenated oils such as hydrogenated sunflower oil, hydrogenated castor oil, hydrogenated copra oil and hydrogenated lanolin; paraffins, microcrystalline waxes, Montan waxes and ozokerites; polyethylene waxes, waxes obtained by Fisher-Tropsch synthesis, waxy copolymers as well as their esters, and silicone waxes such as polyalkoxy- and polyalkylsiloxanes.

The fatty phase may, in addition, comprise additives such as lipophilic cosmetic active agents and/or fat-soluble ingredients which are generally used in cosmetics such as perfumes. Preferably, these additives may be present in a quantity of 0–20% relative to the total weight of the fatty phase.

The present invention also relates to a process for preparing a composition as defined above, in which the pulverulent phase is dispersed in an oil-in-water type emulsion, the dispersion obtained is cast in a mould and the dispersion is freeze-dried.

The dry compact powder obtained may then be optionally removed from the mould.

One advantage of the process according to the invention is that it allows the production of compact powders comprising a high level of fillers, especially incompactible fillers which powders could not be obtained satisfactorily by the prior art processes.

Another advantage of the process according to the invention is that it makes it possible to introduce water-soluble additives into the final composition, via the aqueous phase of the emulsion.

These additives may be, for example, formulation adjuvants or cosmetic active agents.

Among the formulation adjuvants, there may be mentioned thickeners such as natural gums, for example, gum arabic, tragacanth gum, and guar gum; cellulose derivatives, pectins such as derivatives of alginic acid and of carragheen, bentonites and colloidal silicas, polysaccharides, synthetic macromolecules especially containing vinyl or acrylic groups, starchy materials, phosphor related derivatives of hydroxylated aliphatic alcohol, esterified natural or synthetic triglycerides; preservatives such as methylparaben; pH modifying agents such as triethanolamine.

Among the cosmetic active agents, there may be mentioned antioxidants or anti-free radical agents; moisturizers or humectants such as glycerin and collagen; UV-screening agents such as benzophenone.

These water-soluble additives may be present in the final composition in a quantity of 0–20%, preferably 0.5–10%.

A specific and preferred embodiment of the process according to the invention is described below.

According to this preferred embodiment, an oil-in-water type emulsion is prepared in the presence of a surfactant, such as triethanolamine stearate or mixtures of stearic acid and triethanolamine. The quantity of surfactant used is preferably 5–15% relative to the total weight of the dispersion, and at most 30%.

The various constituents of the pulverulent phase are then gradually introduced into the emulsion obtained so as to obtain a dispersion. The dispersion obtained may comprise 0.1–30% of fatty phase, 0.1–65% of pulverulent phase and 30–70% of aqueous phase. Preferably, the dispersion comprises 1–15% of fatty phase, 1–45% of pulverulent phase and 35–55% of aqueous phase.

Before moulding, the dispersion has, preferably, a viscosity of 0.5–30 Pa.s, measured at 25° C. with the aid of a rotational viscometer.

Indeed, when the viscosity is less than 0.5 Pa.s, the composition obtained after drying tends to collapse and to be soft. When the viscosity is greater than 30 Pa.s, there is some difficulty in filling the moulds.

The dispersion is introduced into a mould with a wide variety of shapes: parallelepipedal, cylindrical, spherical, hemispherical, frustoconical or any desired aesthetic shape.

The mould is then introduced into a freeze-drier. The freezing is preferably performed at a very low rate, of the order of 0.5° C./min. down to a temperature below the starting melting temperature of the dispersion which is generally between −15° C. and −5° C., in order to obtain a very fine crystallization of the water.

When the product is completely frozen, there is primary sublimation of the ice crystals; the sublimation pressure is determined by the starting melting temperature of the dispersion, the temperature which should preferably not be exceeded during the freeze-drying cycle so that there is no interstitial melting. Preferably, the sublimation may be performed at a pressure of 40 Pa (0.4 mbar) for a starting melting temperature of about −12° C.

The sublimation proceeds until the last ice crystal has sublimed. At this very moment, the temperature of the product increases because the endothermic phenomenon of sublimation no longer occurs.

The secondary drying stage is thereby reached: at this stage, the pressure is maintained very low, at about 1 Pa and the temperature is brought to about 25° C. in order to evacuate the last traces of water.

The composition is then optionally removed from the mould in the form of a dry compact powder which is obtained.

In general, the composition according to the invention may comprise, after freeze-drying, 2–98% of pulverulent phase, preferably 60–97%, and 2–98% of fatty phase, preferably 3–40%.

In a preferred form of the composition according to the invention, the composition comprises 45–97% of incompactible filler, 0–40% of compactible filler and 3–30% of fatty phase.

The composition thus obtained may therefore be presented in the form of cups, sticks, or cylinders or in any other complex form.

It has the appearance of a customary compacted powder although it was not obtained by compacting with the aid of a mechanical press.

A feature of the present invention is that the fatty (lipid) phase and/or the aqueous thickened phase present in the composition creates a porous network; this network remains present in the composition after freeze-drying is accomplished. Preferably, the composition of the present invention, after freeze-drying, has an internal porosity greater than 2 $m^2/g$, more preferably greater than 3 $m^2/g$, and most preferably from 4 to 100 $m^2/g$.

The present invention is illustrated in greater detail in the following examples, which in no way limit the invention.

EXAMPLE 1

A compact make-up powder having the following composition was prepared:
Pulverulent phase
  Microcapsules of silica (SILICA BEADS 150 from MAPRECOS) . . . 25%
  (incompactible inorganic spherical filler)
  Microcapsules in the form of a vinylidene chloride/acrylonitrile copolymer (EXPANCEL 551 DE from KEMANORD PLAST) . . . 2%
  (incompactible organic spherical filler)
  Pigments (yellow, red and black iron oxides, titanium dioxide) . . . 5%
Fatty phase
  Parleam oil . . . 5%
  Glyceryl stearate . . . 2.2%
  Emulsifier (stearic acid and triethanolamine) . . . 3.3%
Aqueous phase
  Water . . . 57.2%
  Preservative . . . 0.3%

An oil-in-water emulsion was prepared in a conventional manner in a MORITZ type mixer by introducing the fatty phase into the aqueous phase at 80° C. Once formed, the pulverulent phase was gradually introduced, with stirring, so as to obtain a dispersion having a viscosity of 6 Pa.s. The dispersion obtained was placed in moulds which were introduced into a freeze-drier and the temperature was decreased to −40° C. with a freezing rate of 0.5° C./min. When the product was completely frozen, the pressure was adjusted to 40 Pa so as to cause primary sublimation of the ice crystals.

The composition obtained after removing from the mould was in a dry and non-hygroscopic form, with a pleasant feel and exhibited no deformation or surface defect.

The powder could easily be removed for application with the aid of a brush.

EXAMPLE 2

A compact powder having the following composition was prepared as in Example 1:
Pulverulent phase
  Microspheres of copolymers of styrene/divinylbenzene having absorbed 3% squalane (PLASTIC POWDER from TOSHIKI) . . . 10%
  (incompactible organic spherical filler)
  Microcapsules of silica (SILICA BEADS 150 from MAPRECOS) . . . 10%
  (incompactible inorganic spherical filler)
  Mica (compactible lamellar inorganic filler) . . . 10%
  Pigments . . . 5%
Fatty phase
  Parleam oil . . . 5%
  Glyceryl stearate . . . 2.2%
  Emulsifier . . . 3.3%
Aqueous phase
  Water . . . 54.2%
  Preservative . . . 0.3%

The composition was prepared as in Example 1.

After freeze-drying, a dry solid mass was obtained which exhibited no deformation or surface defect and was non-hygroscopic. This compact powder had a smooth feel and the powder could easily be removed with a make-up brush.

EXAMPLE 3 (comparative example)

By way of comparison, a composition containing only an incompactible filler, of the spherical inorganic type, was prepared. This composition comprised:
Pulverulent phase
  Microcapsules of silica (SILICA BEADS 150 from MAPRECOS) . . . 25%

(incompatible inorganic spherical filler)
Pigments . . . 5%
Fatty phase
Parleam oil . . . 5%
Glyceryl stearate . . . 2.2%
Emulsifier . . . 3.3%
Aqueous phase
Water . . . 59.2%
Preservative . . . 0.3%

The composition was prepared as in Example 1.

The compact powder obtained did not exhibit good disintegration; the feel was a lot greasier and it had a tendency to become waxy.

EXAMPLE 4

A compact face powder having the following composition was prepared:
Pulverulent phase
Microcapsules of silica (SILICA BEADS 150 from MAPRECOS) . . . 25%
(incompactible inorganic spherical filler)
Microcapsules in the form of a vinylidene chloride/acrylonitrile copolymer (EXPANCEL 551 DE from KEMANORD PLAST) . . . 2%
(incompactible organic spherical filler)
Pigments . . . 5%
Fatty phase
Parleam oil . . . 5%
Glyceryl stearate . . . 2.2%
Emulsifier . . . 3.3%
Aqueous phase
Water . . . 52.2%
Glycerine . . . 5%
Preservative . . . 0.3%

The composition was prepared in a manner similar to Example 1.

The powder obtained could be easily removed with a make-up brush and was not harsh on the skin.

EXAMPLE 5 (comparative example)

By way of comparison, the composition according to Example 1 was prepared and it was dried by two different means:
at room temperature
in an oven at 60° C.

It was observed that the two products obtained by either of these means were cracked and had a very greasy feel.

As a reminder, in Example 1, in which the drying was performed by freeze-drying, the product obtained was intact and of non-greasy feel.

EXAMPLE 6 (comparative example)

By way of comparison, a composition containing only a lamellar inorganic type filler was prepared. This composition comprised:
Pulverulent phase
Talc . . . 25%
Pigments . . . 5%
Fatty phase
Parleam oil . . . 5%
Glyceryl stearate . . . 2.2%
Emulsifier . . . 3.3%
Aqueous phase
Water . . . 59.2%
Preservative . . . 3%

The composition was prepared as in Example 1.

It was observed that the composition obtained crystallizes into sheets, that is to say had a heterogeneous surface.

Furthermore, it did not disintegrate easily and had a tendency to become waxy.

EXAMPLE 7

A compact powder having the following composition was prepared as in Example 1:
Pulverulent phase
Microcapsules of silica (SILICA BEADS 150 from MAPRECOS) . . . 26 g.
(incompactible inorganic spherical filler)
Microcapsules in the form of a vinylidene chloride/acrylonitrile copolymer (EXPANCEL 551 DE from KEMANORD PLAST) . . . 13.25 g.
(incompactible organic spherical filler)
Mica (compactible lamellar organic filler) . . . 2 g.
Fatty phase
Parleam oil . . . 5 g.
Glyceryl stearate . . . 2.2 g.
Emulsifier . . . 3.3 g.
Aqueous phase . . . 48.25%

After freeze-drying, the internal porosity of the composition was 5 $m^2/g$.

We claim:

1. A composition which has been freeze-dried to form a compact powder comprising a fatty phase and a pulverulent phase, said pulverulent phase comprising a first incompactible filler and at least one second filler, which may be compactible or incompactible, said first and said second fillers being inorganic lamellar fillers, organic lamellar fillers, inorganic spherical fillers, or organic spherical fillers, said first and said second fillers being different types, and wherein the amount of incompactible fillers present in said composition is from about 2–10% relative to the total weight of the composition when said incompactible fillers have a density less than 0.1 $g/cm^3$, and from about 2–40% relative to the total weight of the composition when said incompactible fillers have a density of 0.1–0.5 $g/cm^3$, and from about 30–90% relative to the total weight of the composition when said incompactible fillers have a density greater than 0.5 $g/cm^3$.

2. The composition of claim 1, wherein said composition has an internal porosity greater than 2 $m^2/g$.

3. The composition of claim 1, wherein said composition has an internal porosity ranging from 4 $m^2/g$ to 100 $m^2/g$.

4. The composition of claim 1, wherein said inorganic lamellar fillers are magnesium silicate hydrates, aluminosilicates, clays, aluminium silicate hydrate, boron nitrides, or mica titaniums.

5. The composition of claim 4, wherein said clays are sericites.

6. The composition of claim 1, wherein said organic lamellar fillers are compactible and are powders of tetrafluoroethylene polymers.

7. The composition of claim 1, wherein said organic lamellar filler is incompactible and is lauroyl lysine.

8. The composition of claim 1, wherein said inorganic spherical fillers are compactible and are zinc or titanium oxides, precipitated calcium carbonate, magnesium carbonate or hydrocarbonate, non-porous spherical silica, or hydroxyapatite.

9. The composition of claim 1, wherein said inorganic spherical fillers are incompactible and are microspheres of silica with an open porosity optionally impregnated with a cosmetic active ingredient, microspheres of hollow silica optionally impregnated with a cosmetic active ingredient, or glass or ceramic microcapsules.

10. The composition of claim 1, wherein said organic spherical fillers are compactible and are metallic soaps derived from carboxylic organic acids having 8 to 22 carbon atoms, powders of non-expanded synthetic polymers, powders of synthetic polymers, or powders of organic materials of natural origin.

11. The composition of claim 10, wherein said metallic soaps are derived from carboxylic acids having 12 to 18 carbon atoms.

12. The composition of claim 11, wherein said metallic soaps are zinc, magnesium or lithium stearate, zinc laurate, or magnesium myristate.

13. The composition of claim 1, wherein said organic spherical fillers are incompactible and are microporous microspheres of polymers that are optionally impregnated with cosmetic active agents and microcapsules of polymers that are optionally cross-linked.

14. The composition of claim 1, comprising 2–98% by weight of said pulverulent phase.

15. The composition of claim 1, wherein said pulverulent phase comprises 1–100% of incompactible fillers relative to the pulverulent phase, 0–99% of compactible filler relative to the pulverulent phase, and 0–50% of pigments relative to the total weight of the composition.

16. The composition of claim 15, wherein said pulverulent phase comprises 60–100% of incompactible fillers and 0–40% of compactible filler, said percentages being relative to the pulverulent phase.

17. The composition of claim 1, comprising 45–97% by weight, of incompactible fillers, said percentage being relative to the total weight of the composition.

18. The composition of claim 1, comprising 0–40% by weight, of compactible fillers, said percentage being relative to the total weight of the composition.

19. The composition of claim 1, comprising 2–98% by weight of fatty phase, said percentage being relative to the total weight of the composition.

20. The composition of claim 1, wherein said fatty phase comprises at least one oil, at least one wax of animal, plant, inorganic or synthetic origin, or mixtures of at least one of said wax and at least one of said oil.

21. The composition of claim 1 wherein said incompactible fillers have a density less than 0.1 g/cm³.

22. The composition of claim 1 wherein said incompactible fillers have a density of 0.1–0.5 g/cm³.

23. The composition of claim 1 wherein said incompactible fillers have a density greater than 0.5 g/cm³.

24. The composition of claim 1 further comprising at least one water-soluble additive.

25. The composition of claim 24, wherein said water-soluble additive is a cosmetic agent, said cosmetic agent being an antioxidant, an anti-free radical agent, a moisturizer, a humectant, or a UV-screening agent.

26. The composition of claim 25, wherein said humectant is glycerin or collagen, and wherein said UV-screening agent is benzophenone.

27. The composition of claim 4, wherein said magnesium silicate hydrates are talcs, wherein said aluminosilicates are micas, and wherein said aluminium silicate hydrate is kaolin.

28. The composition of claim 10, wherein said powders of synthetic polymers are powders of silicone resin.

29. A process for preparing a composition according to claim 1 comprising the steps of: preparing an oil-in-water emulsion of said fatty phase in an aqueous phase; dispersing said pulverulent phase in said emulsion; casting said dispersion obtained in a mould; and freeze drying said dispersion.

30. The process according to claim 29, wherein said dispersion obtained before said casting step comprises 0.1–30% of said fatty phase, 0.1–65% of said pulverulent phase, and 30–70% of said aqueous phase.

31. The process according to claim 29, further comprising the step of adding to said aqueous phase at least one formulation adjuvant, at least one cosmetic active agent, or a mixture of at least one formulation adjuvant and at least one cosmetic active agent.

32. The process according claim 29, wherein said dispersion of said pulverulent phase in said emulsion has a viscosity of 0.5–30 Pa.s, measured at 25° C. with the aid of a rotational viscometer.

33. The process according to claim 29, wherein said freeze-drying is performed at a rate of 0.5° C./min. down to a temperature below the starting melting temperature of said dispersion.

* * * * *